(12) United States Patent
Marciniec et al.

(10) Patent No.: US 8,841,473 B2
(45) Date of Patent: Sep. 23, 2014

(54) SYNTHESIS OF FLUOROSILICONES AND THEIR DERIVATIVES

(75) Inventors: Bogdan Marciniec, Swarzedz (PL); Hieronim Maciejewski, Poznan (PL); Izabela Dabek, Poznan (PL); Joanna Karasiewicz, Komorniki (PL)

(73) Assignee: Adam Mickiewicz University, Poznan (PL)

(*) Notice: Subject to any disclaimer, the term of this patent is extended or adjusted under 35 U.S.C. 154(b) by 1 day.

(21) Appl. No.: 13/393,389

(22) PCT Filed: Aug. 16, 2010

(86) PCT No.: PCT/PL2010/000074
§ 371 (c)(1),
(2), (4) Date: Feb. 29, 2012

(87) PCT Pub. No.: WO2011/028143
PCT Pub. Date: Mar. 10, 2011

(65) Prior Publication Data
US 2012/0157703 A1 Jun. 21, 2012

(30) Foreign Application Priority Data

Sep. 1, 2009 (PL) .......................... 388932
Sep. 1, 2009 (PL) .......................... 388933

(51) Int. Cl.
*C07F 7/12* (2006.01)
*C08G 77/385* (2006.01)
*C08G 77/04* (2006.01)
*C07F 7/08* (2006.01)
C08G 77/14 (2006.01)
C08G 77/12 (2006.01)

(52) U.S. Cl.
CPC .............. *C08G 77/385* (2013.01); *C08G 77/14* (2013.01); *C08G 77/12* (2013.01); *C08G 77/045* (2013.01); *C07F 7/0879* (2013.01)
USPC ...................................................... 556/454

(58) Field of Classification Search
None
See application file for complete search history.

(56) References Cited

U.S. PATENT DOCUMENTS 5,639,845 A 6/1997 Inomata et al.
6,114,446 A 9/2000 Narisawa et al.

FOREIGN PATENT DOCUMENTS

| GB | 2 443 626 A | | 5/2008 |
| JP | 09124663 | * | 5/1997 |
| WO | WO 2008/033043 A1 | | 3/2008 |

OTHER PUBLICATIONS

Yaroshi et al., Synthesis of water- and oil-repellent organofluorosilicon compounds. Mendeleev Communication 2006, 16, 190-192.*
Marciniec et al., Hydrosilylation: A Comprehensive Review on Recent Advances. Springer, 2009, 3-51 and 159-189.*
Sabourault et al., Platinum Oxide (PtO2): A Potent Hydrosilylation Catalyst. Organic Letter 2002, 4, 2117-2119.*
Marciniec et al., Catalytic activity of siloxy-rhodium(I) complexes in hydrosilylation of alkene. Journal of Molecular Catalysis A: Chemical 1999, 144, 263-271.*
Casreact printout of foreign patent No. 09124663, published on May 13, 1997).*
Marciniec et al., "Modification of (Poly)Siloxanes via Hydrosilylation Catalyzed by Rhodium Complex in Ionic Liquids," *Monatshefte für Chemie Chemical Monthly*, 2006, pp. 605-611, vol. 137.
Furukawa et al., "Reactivity of Cyclosiloxane with 3,3,4,4,5,5,6,6,6-Nonafluorohexyl Group and Its Application to Fluorosilicone Synthesis," *Journal of Applied Polymer Science*, 2001, pp. 3333-3340, vol. 82.
Furukawa et al., "Synthesis and Properties of Fluorosilicone with Perfluorooctylundecyl Side Chains," *Journal of Polymer Science: Part A: Polymer Chemistry*, 2003, pp. 2704-2714, vol. 41.
Boutevin et al., "Chapter 3: Side Group Modified Polysiloxanes", *Silicon-Containing Polymers: The Science and Technology of Their Synthesis and Applications*, 2000, pp. 79-82 and 96-103, Kluwer Academic Publishers.
Kobayashi et al., "Surface Tension of Poly [(3,3,4,4,5,5,6,6,6-nonafluorohexyl)-methylsiloxane]," *Macromolecules*, 1990, pp. 4929-4933, vol. 23, American Chemical Society.
Li, "Preparation, Characterization and Antifoaming Property of Fluorosilicone Oils with Fluoroalkyloxypropyl Group Substitution," *e-Polymers*, 2008, pp. 1-12, No. 003, http://www.e-polymers.org.
Oct. 20, 2010 Written Opinion issued in International Patent Application No. PCT/PL2010/000074.

(Continued)

*Primary Examiner* — Michael Barker
*Assistant Examiner* — Po-Chih Chen
(74) *Attorney, Agent, or Firm* — Oliff PLC

(57) ABSTRACT

The subject of invention is the method of synthesis of fluorosilicone co-polymers of arbitrary topology and general formula 1 in which among others if A stands for CH—O$(CH_2)_m(CF_2)_n CF_2 H$ group, then the method is based on hydrosilylation reaction of appropriate fluoroalkyl-allyl ether with polyhydrosiloxanes containing at least one Si—H group, catalyzed by siloxide rhodium complex. If A stands for in which Z stands for divalent group either then the method is based on the reaction of nucleophilic opening of oxirane ring in appropriate epoxyfunctional co-polysiloxanes, in acidic environment.

(I)

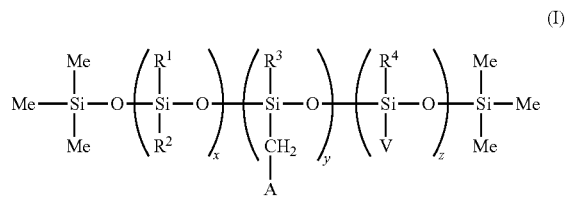

11 Claims, No Drawings

(56) References Cited

OTHER PUBLICATIONS

Oct. 20, 2010 International Search Report issued in International Paten Application No. PCT/PL2010/000074.

Brook, M., "Silicon in Organic. Organometallic and Polymer Chemistry," Wiley, New York. (2000) p. 405.

Horino et al., "Alkene and Diene Hydrosilylations Catalyzed by Lanthanum Tris[bis(trimethylsilyl)amide]" *Organometallics*, vol. 23, (2004) pp. 12-14.

Furukawa et al., "Synthesis of Fluorosilicone Having Highly Fluorinated Side Chains Based on the Hydrosilylation of Fluorinated Olefins with Polyhydromethyisiloxane," *J. Polym. Sci., Part A: Polym. Chem.*, vol. 40 (2002), pp. 3120-3128.

Braun et al.. "C-F Bond Activation of Highly Fluorinated Molecules at Rhodium: From Model Reactions to Catalysis." Europ. J. Inorg. Chem., (2011) pp. 613-625.

Ameduri et al.. "Use of Original Fluorinated Telomers in the Synthesis of Hybrid Silicones," *Fluoropolymers 1: Synthesis*, edited by Hougham et al., Plenum Press, New York (1999), pp. 67-80.

Jurkiewicz et al., "Branched Polymers With Loops." *LPTHE*, Oct. 1996, pp. 1-11.

Ghaouar et al, "Kinetics of phase separation in ramified polymer blends of arbitrary topology" *The European Physical Journal E*, vol. 16, (2005), pp. 409-413.

Dolgushev et al., "Dynamics of semiflexible treelike polymeric networks," *The Journal of Chemical Physics*, vol. 131. (2009), pp. 044905-1-044905-9.

\* cited by examiner

SYNTHESIS OF FLUOROSILICONES AND THEIR DERIVATIVES

The subject of invention is the method of synthesis of fluorosilicone copolymers of an arbitrary topology and the general formula 1

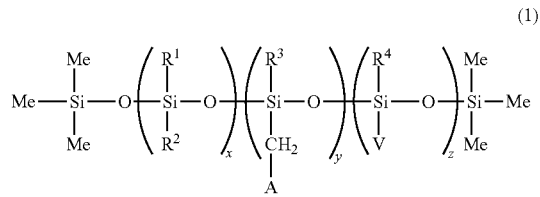

(1)

Organosilicon derivatives containing fluorine are of interest for production of new materials.

Fluorosiloxanes are valuable substrates in many areas of industry because of their unique properties including very low surface tension, chemical inertness, thermal stability, low light refraction index and low friction factor. For example they are used for production of elastomers resistant to organic solvents for automotive industry, as antifoaming agents for organic solvents, as agents modifying friction in lubricants, as optical fibre coating and surface modifiers.

Hitherto three methods of synthesis of fluorosilicones have been used: the first one based on hydrolytic condensation of fluorocarbofunctional dichloroalkylsilanes, the second one based on ring opening polymerisation of cyclic siloxanes containing fluoroalkyl substituents and the third one based on hydrosilylation of fluorinated olefins with poly(hydromethyl, dimethyl)siloxanes. These methods are described in (1).

The British patent GB2443626 and the paper by L. Zhangxiong (2) describe the synthesis of fluorosilicones in the process of hydrolytic condensation of fluoroalkyl-dichlorosilanes. For example, the condensation of trifluoroethyloxy)propyl-methyldichlorosilane was conducted in ethyl acetate environment and in the presence of zinc oxide whose function was to bind chlorine liberated in the process, at 5° C. The products were a mixture of cyclosiloxanes that were distilled from the reaction mixture and small amounts of fluorosilicones of different length chains. At the next stage of the process the ring opening polymerisation of the cyclosiloxanes obtained is performed in the presence of trifluoromethylsulfonic acid as a catalyst. The above multistage and time consuming method does not ensure getting selectively a single product as at the first stage of condensation and at the second stage of polymerisation; mixtures of cyclic and linear fluorosilicones of different length chains are obtained.

Kobayashi (3) proposed the method of obtaining fluorosiloxanes by ring opening polymerisation of cyclic siloxanes 1,3,5-tris(trifluoropropyl)-1,3,5-trimethylocyclotrisiloxane. Furukawa (4) proposed an alternative method based on ring opening polymerisation of 1,3,5-tris(nonafluorohexyl)-1,3,5-trimethylocyclotrisiloxane with trifluoromethylsulfonic acid as a catalyst taking place at 60-100° C. for 12-24 hours. These methods are not selective as lead to a mixture of polysiloxanes of different length chains and not uniform molecular mass. The third group of methods of fluorosiloxane synthesis includes those based on hydrosilylation of fluorinated olefins with polyhydrosiloxanes.

Y. Furukawa (5) describes the synthesis of fluorosilicones by hydrosilylation of heptadecafluoroundecene with poly (hydromethyl, dimethyl)siloxanes containing different amounts of Si—H groups, in the presence of hexachloroplatinic acid as a catalyst at 100° C. On the industrial scale fluorinated olefins are obtained from fluoroalkyl iodide as a precursor, which means that the olefin contains small amount of iodide ions having negative effect on hydrosilylation as they poison the catalyst. In the majority of methods the catalyst is dissolved in the olefin and hydrosiloxane is introduced into this mixture. Therefore, if the iodide ions poison the catalyst, then the reaction does not take place and the mixture of expensive substrates cannot be reused.

The U.S. Pat. No. 5,639,845 describes the method based on addition of polyhydrosiloxane to fluorinated alkenes in the presence of Karstedt catalyst (platinum) in the environment of bis(trifluoromethyl)benzene as a solvent. The reaction is performed at 110° C. for 19-24 h. Fluorinated olefins containing the vinyl group —CH═CH$_2$ react less efficiently than those containing the allyl group —CH$_2$CH═CH$_2$, so the presence of the latter is recommended. Moreover, the solvent had to be removed after the reaction, which implied the need of another stage of the reaction and made the process more complex.

The subject of invention is the cheap and effective method of synthesis of fluorosilicones of an arbitrary topology and the general formula 1

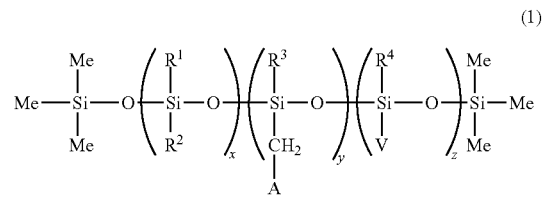

(1)

in which
A stands for a group of formula 2 or 3

$$CH_2 — O(CH_2)_m(CF_2)_nCF_2H \quad (2)$$

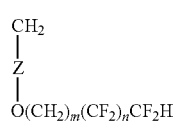

(3)

in which n=1-12 and m=1-4
and if A is a group of formula 2,
then
x=0-100, y=1-50 and z=0;
R$^1$, R$^2$, and R$^3$ can be the same or different and stand for an alkyl group containing C=1-25 or an aryl group,
if A is a group of formula 3,
then
x=0-100, y=1-50, z=0-50,
R$^1$, R$^2$, R$^3$ and R$^4$ can be the same or different and stand for an alkyl group containing C=1-12 or aryl group,
V is an alkyl group containing C=1-12, an aryl group or any organic functional group not reacting with an epoxy group,
Z stands for a divalent group of the formulas

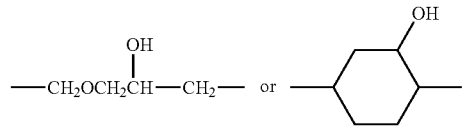

The first version of the method being the subject of this invention is aimed at synthesis of fluorosiloxanes of an arbitrary topology and general formula 1 in which A stands for a group of formula 2, x, y, z and $R^1$, $R^2$, $R^3$ have the meaning specified above for this case, by hydrosilylation of an appropriate fluoroalkyl-allyl ether of general formula 4

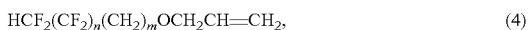

$$HCF_2(CF_2)_n(CH_2)_mOCH_2CH=CH_2, \quad (4)$$

where m=1-4, n=1-12
with polyhydrosiloxanes containing at least one Si—H group and of general formula 5

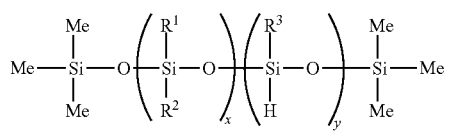

(5)

in which $R^1$, $R^2$, $R^3$ and x, y have the meaning specified above, in the presence of siloxide rhodium complex [{Rh(OSiMe$_3$)(cod)}$_2$] as a catalyst.

The reaction is performed at temperatures from the range 20-150° C., preferably at temperatures from 25 to 60° C., until the reaction completion, which usually takes 0.5-2 hours, in an open system and under atmospheric pressure.

It is recommended but not necessary to use fluoroalkyl-allyl ether in excess over the appropriate polyhydrosiloxane to ensure complete consumption of Si—H groups, as their presence has adverse effect on the stability of the product. The preferable excess of fluoroalkyl-allyl ether is from 1.1 to 1.4 mol per each mol of Si—H groups present in polyhydrosiloxane; the best results are obtained at the excess of 1.1.

The catalyst is applied in the amount from $10^{-4}$ to $10^{-6}$ mol Rh per 1 mol of Si—H groups present in polyhydrosiloxane; the best results are obtained for its amount of $5\times10^{-5}$ mol.

In the first version of the method proposed, an appropriate fluoroalkyl-allyl ether and the catalyst [{Rh(OSiMe$_3$)(cod)}$_2$], in the amount corresponding to the concentration of $10^{-4}$-$10^{-6}$ mol Rh per 1 mol of Si—H groups present in the polyhydrosiloxane, are introduced into the reactor and stirred to get a homogenous system. To the mixture obtained an appropriate polyhydrosiloxane is added dropwise. After introducing the whole load of the polyhydrosiloxane, the content of the reactor is stirred on heating to a temperature from the range 20-150° C. till the reaction completion, which usually takes 1-4 hours. The product obtained can be used directly in many applications but when its high purity is needed the post-reaction mixture is subjected to evaporation of the remains of unreacted fluoroalkyl-allyl ether. When the products are low molecular siloxanes their purification can be made by fractional distillation under reduced pressure and collecting the fraction corresponding to the target product. High-molecular products are purified exclusively by evaporation of the unreacted ether.

The method proposed permits obtaining fluorocarbofunctional polysiloxanes in a single-stage process.

The use of siloxide rhodium complex as a catalyst in the reaction of fluoroalkyl-allyl ether hydrosilylation permitted a reduction of the temperature of the process and shortening its time, hence preventing the occurrence of side reactions (e.g. isomerization of fluoroalkyl-allyl ether) and improving the yield and selectivity of the process. In contrast to the hitherto used platinum catalysts, the rhodium catalysts show greater resistance to poisoning and hence are less susceptible to the impurities contained in the substrates. The siloxide rhodium catalyst permits a single-stage synthesis of various fluorosilicone derivatives with no need to modify the method for each group of derivatives. Fluoroalkyl-allyl ether used is obtained by the Williamson method from fluorinated alcohols that are much more accessible and cheaper than fluoroalkyl iodides used in the earlier proposed methods.

The second version of the method being the subject of this invention is aimed at synthesis of fluorosiloxanes of an arbitrary topology and general formula 1 in which A stands for a group of formula 3; x, y, z and $R^1$, $R^2$, $R^3$, $R^4$, V and Z have the meaning specified above for this case, is aimed at the nucleophilic opening of the oxirane ring in the appropriate epoxyfunctional co-polysiloxanes of an arbitrary topology and general formula 6

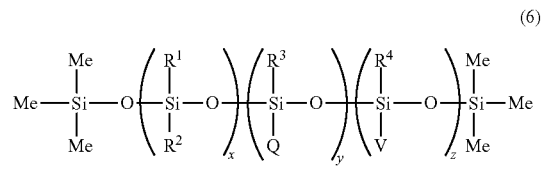

(6)

where $R^1$, $R^2$, $R^3$, $R^4$, V and x, y, z have the meaning specified above and Q is the glycidyloxypropyl group of formula 7 or the 2-(3,4-epoxycyclohexyl)ethyl group of formula 8

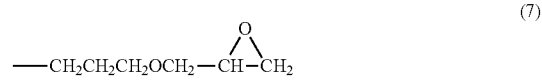

(7)

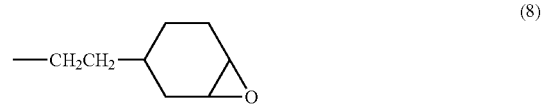

(8)

with the help of fluorinated alcohols of general formula 9

$$HO(CH_2)_m(CF_2)_nCF_2H \quad (9)$$

in which n and m take the above specified values, in acidic environment of pH from 1 to 4.5. The desired pH value is achieved by addition of any inorganic or organic acids. The use of orthophosphoric acid is most recommended.

The process is performed in a single stage in an open system and under atmospheric pressure. The appropriate epoxyfunctional siloxane and fluorinated alcohol are introduced into the reactor, in the amounts corresponding to the ratio of 0.1-1 mol of the fluorinated alcohol per each mol of the epoxy groups contained in the epoxyfunctional siloxane used. The substrates are stirred. To the mixture obtained the selected acid is introduced until getting pH from the range 1-4.5, preferably 2-4. Then the content of the reactor is heated to temperatures from the range 80-130° C., till the reaction completion, which usually takes 1-4 h.

The equimolar amounts of the reagents ensure full consumption of epoxy groups, while introduction of smaller amounts of fluorinated alcohol permits obtaining polysiloxanes with mixed groups (fluorocarbofunctional and epoxyfunctional). By choosing the ratio of the reagents it is possible to control the contents of the epoxy and fluorocarbofunctional groups in the polysiloxane chains to meet the specific needs of particular application. The presence of epoxy groups besides fluorocarbofunctional ones permits further transformations of these epoxy groups into hybrid materials or curing by chemical or photochemical methods.

The method being the subject of this invention is based on the opening of oxirane ring in the epoxyfunctional siloxanes with the help of fluorinated alcohols in acidic environment. In the hitherto known methods of synthesis of fluorosilicones, the substrates were fluorinated olefins, which are not only hardly accessible and expensive but also contain impurities that can poison the hydrosilylation catalysts used. In the method proposed the substrates are fluorinated alcohols that are much cheaper and easier accessible and their possible impurities have no influence on the catalysts used. The opening of oxirane ring is catalysed by acids, which are much cheaper and are not poisoned in contrast to the transient metal compounds used in hydrosilylation. The catalysts can be various inorganic and organic acids that would permit getting pH=1-4.5. In this pH range the opening of oxirane ring is effective and with high yield. The most recommended is orthophosphoric acid, which is cheap and ensures the pH desired. The epoxyfunctional (poly)siloxanes used in the method presented can be easily obtained with high yield by the method described in PL-198290 or P-380737, and many of them are produced on industrial scale. The synthesis which is the subject of this invention is illustrated by the following examples that do not limit the scope of its application.

EXAMPLE I

Portions of 15 g (45 mmol) of 3-(glycidyloxypropyl)-1,1,1,3,5,5,5-heptamethyltrisiloxane and 10.4 g (45 mmol) of octafluoropentyl alcohol were placed in a flask equipped with a magnetic stirrer and reflux. Then 35 μl of orthophosphoric acid $H_3PO_4$ was added. The content of the flask was heated to 80° C. and kept at this temperature for 2 hours on stirring. The course of the reaction was chromatographically controlled. After the time of 2 hours the substrates were observed to disappear and one product was formed. The product was clear, bright yellow 3-[3-{3-octafluoropentyloxy-2-hydroxypropoxy}propyl]heptamethyltrisiloxane in the amount of 23.1 g, which corresponds to the yield of 99%. The identity of the product was confirmed by NMR analysis.

$^1$H NMR (C6D6, 298K, 300 MHz) δ (ppm): 0.05 (3H, —SiCH3); 0.14 (18H, —Si(CH3)3); 0.56 (2H, —SiCH2-); 1.69 (2H, —CH2-); 3.25 (2H, —CHCH2O—); 3.48 (1H, —OH); 3.54 (2H, —CH2CF2); 3.68 (1H, —CH—); 4.81 (4H, —CH2O); 5.44 (1H, —CF2H)

$^{13}$C NMR (C6D6, 298K, 75.5 MHz) δ (ppm): −0.21 (—OSiCH3O—); 1.96 (—OSi(CH3)); 13.91 (—SiCH2-); 23.65 (—CH2-); 70.05 (—CH—); 71.02 (—OCH2-); 72.30 (—CH2O—); 74.28 (—CH2O—); 105.18, 108.55, 111.91 (—CF2-); 119.49 (—CF2H)

$^{29}$Si NMR(C6D6, 298K, 59.6 MHz) δ (ppm): −21.92 (—OSiCH3O—); 7.36 (Si(CH3)3)

EXAMPLE II

Synthesis was performed as in example I, but instead of 3-(glycidyloxypropyl)-1,1,1,3,5,5,5-heptamethyltrisiloxane the amount of 15.5 g (45 mmol) of 3-{2-(3,4-epoxycyclohexyl)ethyl}+1,1,1,3,5,5,5-heptamethyltrisiloxane was used. The product was clear and yellow 3-{2-(3-hydroxy-4-octafluoropentoxy-cyclohexyl)ethyl}-heptamethyltrisiloxane in the amount of 23.9 g, which corresponds to the yield of 98%. The identity of the product was confirmed by NMR analysis.

$^1$H NMR(C6D6, 298K, 300 MHz) δ (ppm): 0.02 (3H, —SiCH3); 0.05 (18H, —Si(CH3)3); 0.56 (2H, —SiCH2-); 0.75-1.85 (18H, cyclo-hexylo), 3.23 (2H, —CHO—); 3.72 (1H, —OH); 3.54 (2H, —CH2CF2); 4.85 (4H, —CH2O); 5.34 (1H, —CF2H)

EXAMPLE III

Synthesis was performed as in example I but instead of octafluoropentyl alcohol, a portion of 5.9 g (45 mmol) of tetrafluoropropyl alcohol was added. The reaction was conducted at 80° C. for 1 hour. The product was 3-[3-{3-tetrafluoropropoxy-2-hydroxypropoxy}propyl]heptamethyltrisiloxane in the amount of 19.6 g, which makes 94% of the theoretical yield.

EXAMPLE IV

Synthesis was conducted as in example I but instead of octafluoropentyl alcohol, a portion of 14.9 g (45 mmol) of dodecafluoroheptyl alcohol was added. The reaction was performed at 120° C. for 4 hours. The product was 3-[3-{3-dodecafluoroheptyloxy-2-hydroxypropoxy}propyl]heptamethyltrisiloxane obtained in the amount of 26.9 g, which makes 90% of the theoretical yield.

EXAMPLE V

Portions of 8.2 g (1 mmol) poly{(glycidyloxypropyl)methyl, dimethyl)siloxane described by formula 2 with x=50, y=25 and 5.8 g (25 mmol) of octafluoropentyl alcohol were placed in a flask equipped with a magnetic stirrer and reflux. Then 35 μl of orthophosphoric acid $H_3PO_4$ was added. The content of the flask was heated to 120° C. and kept at this temperature for 4 hours on stirring. The course of the reaction was controlled by FT-IR analysis; the loss of intensity of the band at 980 cm$^{-1}$ assigned to the epoxy group was compared. The product was clear and bright yellow poly([3-{3-octafluoropentyloxy-2-hydroxypropoxy}propyl]methyl, dimethyl)siloxane, described by formula 1 with x=50, y=25 of high viscosity and in the amount of 13.9 g, which corresponds to 99% theoretical yield. The identity of the product was confirmed by FT-IR and NMR results.

FT-IR: 1011 cm$^{-1}$ (Si—O—Si), 1259 cm$^{-1}$ (Si—CH$_3$), 2961 cm$^{-1}$ (CH$_2$CH$_2$CH$_2$), 3446 cm$^{-1}$ (—OH), disappearance of the band assigned to epoxy groups and occurring at 912 cm$^{-1}$ $^1$H NMR (CD3OD, 298K, 300 MHz) δ (ppm): 0.06 (m, —OSi(CH$_3$)—), 0.56 (m, —SiCH$_2$—), 1.56 (m, —SiCH$_2$CH$_2$—), 3.23-3.33 (m, —CH$_2$O—), 3.47 (m, —CH$_2$OCH$_2$—), 3.89 (m, CH(OH)), 5.9-6.3 (tt, CF$_2$H); disappearance of the signals assigned to epoxy groups at 2.58-2.75 ppm.

EXAMPLE VI

Synthesis was performed as in example V but instead of poly{(glycidyloxypropyl)methyl, dimethyl)siloxane a potion of 8.5 g (1 mmol) of poly({2-(3,4-epoxycyclohexyl)ethyl}methyl, dimethyl)siloxane described by formula 2 with x=50, y=25 was used. The product was poly(3-{2-(3-hydroxy-4-octafluoro-pentoxy-cyclohexyl)ethyl}methyl, dimethyl)siloxane described by formula 1 in the amount of 12.9 g with x=50, y=25, which makes 91% of the theoretical yield.

EXAMPLE VII

Synthesis was performed as in example V but instead of poly{(glycidyloxypropyl)methyl, dimethyl)siloxane a portion of 11.3 g (1 mmol) of poly{(glycidyloxypropyl)methyl, phenylmethyl)siloxane described by formula 2 with x=50, y=25 was used. The product was poly([3-{3-octafluoropentyloxy-2-hydroxypropoxy}propyl]-methyl, phenylmethyl)siloxane described by formula 1 with x=50, y=25 in the amount of 15.1 g, which makes 88% of the theoretical yield.

EXAMPLE VIII

Portions of 14.7 g (1 mmol) poly{(glycidyloxypropyl)methyl, dimethyl)siloxane described by formula 2 with x=100, y=50 and 11.6 g (50 mmol) of octafluoropentyl alcohol were placed in a flask equipped with a magnetic stirrer and reflux. Then 70 μl of orthophosphoric acid $H_3PO_4$ was added. The content of the flask was heated to 140° C. and kept at this temperature for 4 hours on stirring. The course of the reaction was controlled by FT-IR analysis, comparing the loss of intensity of the band assigned to the epoxy group, present at 912 cm$^{-1}$. The product was clear poly([3-{3-octafluoropentyloxy-2-hydroxypropoxy}propyl]methyl, dimethyl)siloxane, described by formula 1, with x=100, y=50, showing very high viscosity, in the amount of 22.3 g, which corresponds to the theoretical yield of 85%. The identity of the product was confirmed by NMR analysis.

$^1$H NMR (CD3OD, 298K, 300 MHz) δ (ppm): 0.05 (m, —OSi(CH$_3$)—), 0.48 (m, —SiCH$_2$—) 1.54 (m, —SiCH$_2$CH$_2$—), 3.41 (m, —CH$_2$O—), 3.56 (m, —CH$_2$OCH$_2$—), 4.02 (m, CH(OH)), 5.9-6.3 (tt, CF$_2$H); disappearance of the signals assigned to epoxy groups at 2.58, 2.76 and 2.62 ppm.

EXAMPLE IX

Portions of 9.5 g (1 mmol) of poly({2-(3,4-epoxycyclohexyl)ethyl}methyl, dimethyl)siloxane described by formula 2, with x=82, y=18 and 4.9 g (18 mmol) of octafluoropentyl alcohol were placed in a flask equipped with a magnetic stirrer and reflux. Then 35 μl of orthophosphoric acid $H_3PO_4$ was added. The content of the flask was heated to 130° C. and kept at this temperature for 4 hours on stirring. The course of the reaction was controlled by FT-IR by observing the loss of intensity of the band assigned to epoxy group, present at 930 cm$^{-1}$. The product was clear poly(3-{2-(3-hydroxy-4-octafluoropentoxy-cyclohexyl)ethyl}methyl, dimethyl)siloxane described by formula 1, with x=82, y=18, showing very high viscosity, in the amount of 13.7 g, which corresponds to the theoretical yield of 95%.

EXAMPLE X

Portions of 20.4 g (75 mmol) of octafluoropentyl-allyl ether and 0.22 μg (10$^{-5}$ mol Rh/1 mol Si—H) of siloxide rhodium complex [{Rh(OSiMe$_3$)(cod)}$_2$ were placed in a flask equipped with a magnetic stirrer, reflux and dropping funnel. Then 15.5 g (70 mmol) of heptamethyltrisiloxane was introduced dropwise to the flask on stirring its contents. After introducing the whole load of silane the contents of the flask were stirred for 1 hour at 25° C. The post-reaction mixture was subjected to distillation under reduced pressure and the fraction boiling at 108-110° C./2 mmHg was collected. The product was 3-(octafluoropentyloxypropyl)-heptamethyltrisiloxane in the amount of 32.8 g, which makes 95% of the theoretical yield.

EXAMPLE XI

Synthesis was conducted as in example X but instead of octafluoropentyl-allyl ether a portion of 12.9 g (75 mmol) of tetrafluoropropyl-allyl ether was added. After completion of the reaction the post-reaction mixture was subjected to distillation under reduced pressure and the fraction boiling at 90-92° C./2 mm Hg was collected. The product was 3-(tetrafluoropropoxypropyl)-heptamethyltrisiloxane obtained in the amount of 26.7 g, which corresponds to 94% of the theoretical yield.

EXAMPLE XII

Portions of 53.6 g (10 mmol) of poly(hydromethyl, dimethyl)siloxane Me$_3$Si-[OSiMe$_2$]$_{50}$—[OSiMeH]$_{25}$—OSiMe$_3$, 74.8 g (275 mmol) of octafluoropentyl-allyl ether and 5.5 μg (10$^{-5}$ mol Rh/1 mol Si—H) of siloxy rhodium complex [{Rh(OSiMe$_3$)(cod)}$_2$] were placed in a flask equipped with a magnetic stirrer and reflux. The content was heated to 60° C. and kept at this temperature for 4 hours on stirring. After this time, the excess of octafluoropentyl-allyl ether was evaporated. FT-IR analysis confirmed total conversion of Si—H evidenced by the disappearance of the band at 2180 cm$^{-1}$. The product was poly({octafluoropentyloxypropyl}methyl, dimethyl)siloxane (x=50, y=25) obtained in the amount of 121 g, which corresponds to 99% of the theoretical yield. The identity of the product was confirmed by NMR analysis.

$^1$H NMR (CD3OD, 298K, 300 MHz) δ (ppm): 0.03 (m, —OSi(CH$_3$)—), 0.66 (m, —SiCH$_2$—), 1.48 (m, —SiCH$_2$CH$_2$—), 3.28-3.38 (m, —CH$_2$O—), 3.52 (m, —CH$_2$OCH$_2$—), 6.0-6.4 (tt, CF$_2$H);

EXAMPLE XIII

Synthesis was performed as in example XII but poly(hydromethyl, phenylmethyl)-siloxane Me$_3$Si—[OSiMe$_2$]$_{82}$—[OSiPhH]$_{18}$—OSiMe$_3$, 86.7 g (10 mmol) was used to which 53.8 g (198 mmol) of octafluoropentyl-allyl ether was added. The product was poly({octafluoropentyloxypropyl}methyl, methylphenyl)siloxane (x=82, y=18) obtained in the amount of 134.5 g, which corresponds to 99% of the theoretical yield. The identity of the product was confirmed by NMR analysis.

$^1$H NMR (CD3OD, 298K, 300 MHz) δ (ppm): 0.05 (m, —OSi(CH$_3$)—), 0.54 (m, —SiCH$_2$—), 1.67 (m, —SiCH$_2$CH$_2$—), 3.34-3.48 (m, —CH$_2$O—), 3.73 (m, —CH$_2$OCH$_2$—), 5.9-6.3 (tt, CF$_2$H); 7.80 (d, Ph), 7.50-7.61 (m, Ph)

LIST OF REFERENCES

1. R. G. Jones, J. Chojnowski, W. Ando, Silicon-Containing Polymers, Kluwer, Dordrecht, 2000).
2. L. Zhang-xiong e-Polymers, 3 (2008) 1
3. H. Kobayashi, M. Owen, Macromolecules, 23, (1990) 4929
4. Y. Furukawa, s. Shin-Ya, H. Miyake, H. Kishino, M. Yamada, H. Kato, M. Sato, J. Appl. Polym. Sci., 82, (2001), 3333)
5. Y. Furukawa, T. Yoneda, J. Polym. Sci., A: Polym Chem., 41 (2003), 2704)

The invention claimed is:
1. A method of synthesis of fluorosilicone copolymers of an arbitrary topology and general formula 1a

(1a)

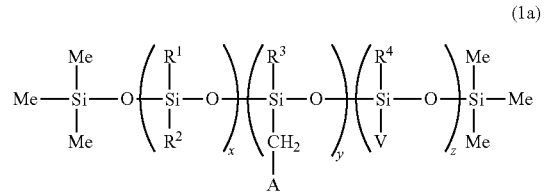

wherein
x=0-100, y=1-50, z=0-50,
$R^1$, $R^2$, $R^3$ and $R^4$ can be the same or different and stand for an alkyl group containing C=1-12 or aryl group
V is an alkyl group containing C=1-12, an aryl group or any organic functional group not reacting with an epoxy group, A stands for a group of formula 3

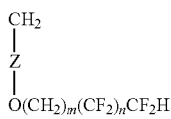
(3)

wherein n=1-12, m=1-4, Z stands for a divalent group either

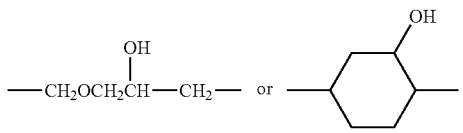

the method comprising a reaction of a nucleophilic opening of an oxirane ring in epoxyfunctional co-polysiloxanes of an arbitrary topology and general formula 6

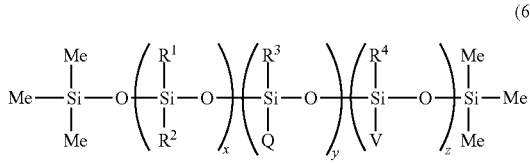
(6)

wherein $R^1$, $R^2$, $R^3$, $R^4$, V, x, y and z have the meaning specified above and Q is the glycidyloxypropyl group of formula 7

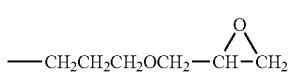
(7)

or a 2-(3,4-epoxycyclohexyl)ethyl group of formula 8,

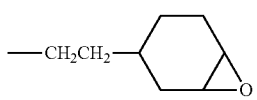
(8)

using fluorinated alcohols of general formula 9

(9)

wherein n and m have the meaning specified above, in an acidic medium of a pH ranging from 1 to 4.5.

2. The method of synthesis as in claim 1 wherein the reaction is performed at the pH range of from 2 to 4.

3. The method of synthesis as in claim 1 wherein the acidic medium comprises inorganic or organic acids.

4. The method of synthesis as in claim 3 wherein the acidic medium comprises orthophosphoric acid.

5. The method of synthesis as in claim 1 wherein the reaction is performed at a temperature from a range of 80-130° C.

6. The method of synthesis as in claim 2 wherein the acidic medium comprises inorganic or organic acids.

7. The method of synthesis as in claim 2 wherein the reaction is performed at a temperature from a range of 80-130° C.

8. The method of synthesis as in claim 3 wherein the reaction is performed at a temperature from a range of 80-130° C.

9. The method of synthesis as in claim 6 wherein the reaction is performed at a temperature from a range of 80-130° C.

10. The method of synthesis as in claim 4 wherein the reaction is performed at a temperature from a range of 80-130° C.

11. The method of synthesis as in claim 1, wherein the method consists of the reaction of the nucleophilic opening of an oxirane ring in epoxyfunctional co-polysiloxanes of an arbitrary topology and general formula 6

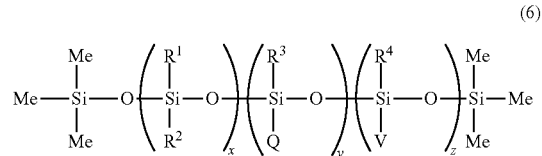
(6)

wherein $R^1$, $R^2$, $R^3$, $R^4$, V, x, y and z have the meaning specified above and Q is the glycidyloxypropyl group of formula 7

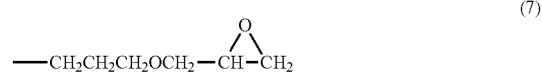
(7)

or a 2-(3,4-epoxycyclohexyl)ethyl group of formula 8,

(8)

using fluorinated alcohols of general formula 9

(9)

wherein n and m have the meaning specified above, in an acidic medium of a pH ranging from 1 to 4.5.

* * * * *